United States Patent
Larsen et al.

(10) Patent No.: US 8,140,370 B2
(45) Date of Patent: Mar. 20, 2012

(54) SYSTEM AND METHOD FOR REDUCING THE STEPS INVOLVED IN SEARCHING FOR AVAILABLE APPOINTMENT TIMES AND SCHEDULING APPOINTMENTS IN A HEALTH CARE ENVIRONMENT

(75) Inventors: Steven J. Larsen, Cross Plains, WI (US); David E. Fuhrmann, Madison, WI (US)

(73) Assignee: Epic Systems Corporation, Verona, WI (US)

( * ) Notice: Subject to any disclaimer, the term of this patent is extended or adjusted under 35 U.S.C. 154(b) by 1856 days.

(21) Appl. No.: 11/099,334

(22) Filed: Apr. 5, 2005

(65) Prior Publication Data

US 2006/0161468 A1 Jul. 20, 2006

Related U.S. Application Data

(60) Provisional application No. 60/645,809, filed on Jan. 20, 2005.

(51) Int. Cl.
   *G06Q 10/00* (2006.01)
(52) U.S. Cl. ............... 705/7.19; 705/7.13; 705/7.14; 705/7.16; 705/7.18; 705/7.24
(58) Field of Classification Search .................. None
   See application file for complete search history.

(56) References Cited

U.S. PATENT DOCUMENTS

| | | | |
|---|---|---|---|
| 4,591,974 A | 5/1986 | Dornbush et al. | |
| 4,667,292 A | 5/1987 | Mohlenbrock et al. | |
| 4,839,806 A | 6/1989 | Goldfischer et al. | |
| 4,893,270 A | 1/1990 | Beck et al. | |
| 4,962,475 A | 10/1990 | Hernandez et al. | |
| 5,065,315 A | 11/1991 | Garcia | |
| 5,072,383 A | 12/1991 | Brimm et al. | |
| 5,072,412 A | 12/1991 | Henderson, Jr. et al. | |
| 5,072,838 A | 12/1991 | Price, Jr. et al. | |
| 5,077,666 A | 12/1991 | Brimm et al. | |
| 5,088,981 A | 2/1992 | Howson et al. | |

(Continued)

FOREIGN PATENT DOCUMENTS

WO   WO 96/27163   9/1996

(Continued)

OTHER PUBLICATIONS

IDX Flowcast eSeries Q & A Version 1.0. Dec. 19, 2003.*

(Continued)

*Primary Examiner* — Lynda Jasmin
*Assistant Examiner* — Brett Feeney
(74) *Attorney, Agent, or Firm* — Bell & Manning, LLC

(57) ABSTRACT

A system and method for searching for and scheduling appointments in a health care environment. The present invention is a computerized searching and scheduling system and method for scheduling appointments. The computerized searching and scheduling system and method comprises a plurality of search definitions for defining a plurality of standard searches based on health care provider pools, date offsets and time ranges. The plurality of search definitions define a plurality of appointment visits that are available for scheduling appointments. The computerized searching and scheduling system and method further comprises a plurality of scheduling algorithms for determining a scheduling solution based on parameters and rules by visit type, procedure, providers, and/or resources. Execution of the plurality of search algorithms provides a plurality of available appointment time options for selection in scheduling an appointment.

65 Claims, 6 Drawing Sheets

U.S. PATENT DOCUMENTS

| | | | |
|---|---|---|---|
| 5,101,476 A | 3/1992 | Kukla | |
| 5,253,362 A | 10/1993 | Nolan et al. | |
| 5,301,105 A | 4/1994 | Cummings, Jr. | |
| 5,319,543 A | 6/1994 | Wilhelm | |
| 5,325,478 A | 6/1994 | Shelton et al. | |
| 5,347,578 A | 9/1994 | Duxbury | |
| 5,361,202 A | 11/1994 | Doue | |
| 5,428,778 A | 6/1995 | Brookes | |
| 5,450,593 A | 9/1995 | Howell | |
| 5,467,268 A * | 11/1995 | Sisley et al. | 705/9 |
| 5,471,382 A | 11/1995 | Tallman et al. | |
| 5,546,580 A | 8/1996 | Seliger et al. | |
| 5,557,515 A | 9/1996 | Abbruzzese et al. | |
| 5,574,828 A | 11/1996 | Hayward et al. | |
| 5,596,752 A | 1/1997 | Knudsen et al. | |
| 5,603,026 A | 2/1997 | Demers et al. | |
| 5,666,492 A | 9/1997 | Rhodes et al. | |
| 5,692,125 A | 11/1997 | Schloss et al. | |
| 5,724,584 A | 3/1998 | Peters et al. | |
| 5,740,800 A | 4/1998 | Hendrickson et al. | |
| 5,748,907 A * | 5/1998 | Crane | 705/2 |
| 5,751,958 A | 5/1998 | Zweben et al. | |
| 5,758,095 A | 5/1998 | Albaum et al. | |
| 5,760,704 A | 6/1998 | Barton et al. | |
| 5,772,585 A | 6/1998 | Lavin et al. | |
| 5,774,650 A | 6/1998 | Chapman | |
| 5,778,346 A | 7/1998 | Frid-Nielsen et al. | |
| 5,781,442 A | 7/1998 | Engleson et al. | |
| 5,781,890 A | 7/1998 | Nematbakhsh et al. | |
| 5,802,253 A | 9/1998 | Gross et al. | |
| 5,823,948 A | 10/1998 | Ross, Jr. et al. | |
| 5,832,450 A | 11/1998 | Myers et al. | |
| 5,833,599 A | 11/1998 | Schrier et al. | |
| 5,838,313 A | 11/1998 | Hou et al. | |
| 5,842,976 A | 12/1998 | Williamson | |
| 5,845,253 A | 12/1998 | Rensimer et al. | |
| 5,848,393 A | 12/1998 | Goodridge et al. | |
| 5,848,395 A | 12/1998 | Edgar et al. | |
| 5,850,221 A | 12/1998 | Macrae et al. | |
| 5,867,688 A | 2/1999 | Simmon et al. | |
| 5,867,821 A | 2/1999 | Ballantyne et al. | |
| 5,899,998 A | 5/1999 | McGauley et al. | |
| 5,907,829 A | 5/1999 | Kida | |
| 5,915,240 A | 6/1999 | Karpf | |
| 5,924,074 A | 7/1999 | Evans | |
| 5,929,851 A | 7/1999 | Donnelly | |
| 5,946,659 A | 8/1999 | Lancelot et al. | |
| 5,960,406 A | 9/1999 | Rasansky et al. | |
| 5,970,466 A * | 10/1999 | Detjen et al. | 705/7.19 |
| 5,974,389 A | 10/1999 | Clark et al. | |
| 5,983,210 A | 11/1999 | Imasaki et al. | |
| 5,987,498 A | 11/1999 | Athing | |
| 5,997,476 A | 12/1999 | Brown | |
| 5,999,916 A | 12/1999 | Peters et al. | |
| 6,014,631 A | 1/2000 | Teagarden et al. | |
| 6,016,477 A | 1/2000 | Ehnebuske et al. | |
| 6,021,404 A | 2/2000 | Moukheibir | |
| 6,029,138 A | 2/2000 | Khorasani et al. | |
| 6,037,940 A | 3/2000 | Schroeder et al. | |
| 6,047,259 A | 4/2000 | Campbell et al. | |
| 6,063,026 A | 5/2000 | Schauss et al. | |
| 6,067,523 A | 5/2000 | Bair et al. | |
| 6,081,786 A | 6/2000 | Barry et al. | |
| 6,082,776 A | 7/2000 | Feinberg | |
| 6,139,494 A | 10/2000 | Cairnes | |
| 6,154,726 A | 11/2000 | Rensimer et al. | |
| 6,182,047 B1 | 1/2001 | Dirbas | |
| 6,185,689 B1 | 2/2001 | Todd | |
| 6,188,988 B1 | 2/2001 | Barry et al. | |
| 6,263,330 B1 | 7/2001 | Bessette | |
| 6,272,593 B1 | 8/2001 | Dujari | |
| 6,275,150 B1 | 8/2001 | Mandler et al. | |
| 6,283,761 B1 | 9/2001 | Joao | |
| 6,289,368 B1 | 9/2001 | Dentler et al. | |
| 6,304,905 B1 | 10/2001 | Clark | |
| 6,317,719 B1 | 11/2001 | Schrier et al. | |
| 6,332,167 B1 | 12/2001 | Peters et al. | |
| 6,345,260 B1 * | 2/2002 | Cummings et al. | 705/8 |
| 6,381,615 B2 | 4/2002 | Gaither | |
| 6,389,454 B1 * | 5/2002 | Ralston et al. | 709/204 |
| 6,401,072 B1 | 6/2002 | Haudenschild et al. | |
| 6,415,275 B1 | 7/2002 | Zahn | |
| 6,567,807 B1 | 5/2003 | Robles et al. | |
| 6,668,256 B1 * | 12/2003 | Lynch | 707/101 |
| 6,678,698 B2 | 1/2004 | Fredell | |
| 6,691,157 B2 | 2/2004 | Muir et al. | |
| 6,725,200 B1 | 4/2004 | Rost | |
| 6,757,898 B1 | 6/2004 | Ilsen et al. | |
| 6,792,087 B2 | 9/2004 | Abdoh | |
| 6,856,989 B1 | 2/2005 | Zhou | |
| 6,988,128 B1 * | 1/2006 | Alexander et al. | 709/206 |
| 7,080,025 B2 * | 7/2006 | Mifune et al. | 705/9 |
| 7,337,123 B2 * | 2/2008 | Dvorak et al. | 705/8 |
| 7,533,083 B2 * | 5/2009 | Aoki et al. | 705/7.19 |
| 7,693,594 B2 * | 4/2010 | von Helmolt et al. | 700/100 |
| 2001/0016056 A1 | 8/2001 | Westphal et al. | |
| 2001/0016853 A1 | 8/2001 | Kucala | |
| 2001/0049610 A1 | 12/2001 | Hazumi | |
| 2001/0051888 A1 | 12/2001 | Mayhak, Jr. et al. | |
| 2001/0056433 A1 | 12/2001 | Adelson et al. | |
| 2002/0001375 A1 | 1/2002 | Alcott et al. | |
| 2002/0001387 A1 | 1/2002 | Dillon | |
| 2002/0002473 A1 | 1/2002 | Schrier et al. | |
| 2002/0002535 A1 | 1/2002 | Kitchen et al. | |
| 2002/0007287 A1 | 1/2002 | Straube et al. | |
| 2002/0062229 A1 | 5/2002 | Alban et al. | |
| 2002/0103673 A1 * | 8/2002 | Atwood | 705/2 |
| 2002/0116220 A1 | 8/2002 | Glazier | |
| 2002/0188478 A1 | 12/2002 | Breeland et al. | |
| 2003/0028402 A1 * | 2/2003 | Ulrich et al. | 705/3 |
| 2003/0061072 A1 | 3/2003 | Baker et al. | |
| 2003/0110059 A1 | 6/2003 | Janas, III et al. | |
| 2003/0200726 A1 | 10/2003 | Rast | |
| 2004/0019501 A1 * | 1/2004 | White et al. | 705/2 |
| 2004/0059714 A1 * | 3/2004 | Larsen et al. | 707/1 |
| 2004/0158486 A1 * | 8/2004 | Nudd et al. | 705/8 |
| 2004/0249676 A1 * | 12/2004 | Marshall et al. | 705/2 |
| 2005/0055252 A1 * | 3/2005 | Todd | 705/5 |
| 2005/0234741 A1 * | 10/2005 | Rana et al. | 705/2 |
| 2006/0026051 A1 * | 2/2006 | Rose | 705/8 |
| 2006/0047553 A1 * | 3/2006 | Fuhrmann et al. | 705/8 |
| 2006/0047554 A1 * | 3/2006 | Larsen et al. | 705/8 |
| 2006/0122865 A1 * | 6/2006 | Preiss et al. | 705/2 |
| 2006/0143044 A1 * | 6/2006 | Conry et al. | 705/2 |
| 2006/0143060 A1 * | 6/2006 | Conry et al. | 705/8 |

FOREIGN PATENT DOCUMENTS

| | | |
|---|---|---|
| WO | WO 9627163 | 9/1996 |
| WO | WO 98/13783 | 4/1998 |
| WO | WO 9813783 | 4/1998 |
| WO | WO 99/22330 | 5/1999 |
| WO | WO 9922330 | 5/1999 |
| WO | WO 99/41682 | 8/1999 |
| WO | WO 9941682 | 8/1999 |
| WO | WO 99/44162 | 9/1999 |
| WO | WO 9944162 | 9/1999 |
| WO | WO 99/63473 | 12/1999 |
| WO | WO 9963473 | 12/1999 |
| WO | WO 00/28460 | 5/2000 |
| WO | WO 00/29983 | 5/2000 |
| WO | WO 0028460 | 5/2000 |
| WO | WO 0029983 | 5/2000 |
| WO | WO 00/65522 | 11/2000 |
| WO | WO 0065522 | 11/2000 |
| WO | WO 02/29664 | 4/2002 |
| WO | WO 0229664 | 4/2002 |

OTHER PUBLICATIONS

FlowCast Master Schedule Training WEB 4.0. Dec. 1, 2005, training for software released Mar. 2004.*

"Sunrise Knowledge-Based Orders," Advanced Clinical Solutions, Eclipsys, www.eclipsys.com, Dec. 2002, 4 pages.

"Sunrise Clinical Manager," Advanced Clinical Solutions, Eclipsys, www.eclipsys.com, Dec. 2002, 4 pages.

"News & events," Eclipsys, www.eclipsys.com, Apr. 16, 2002, 3 pages.

"Horizon Clinicals," McKesson Corporation, www.mckesson.com, 2003, 2 pages.

"Acute Care EMR—Solutions," Cerner Corporation, www.cerner.com, 2002-2003, 2 pages.

"Foundation," IDX Systems Corporation, www.idx.com, 1999-2004, 2 pages.

"Supporting the Work of Clinicians," IDX Systems Corporation, www.idx.com, 1999-2004, 1 page.

"Autonomy Update™," production brief, 2 pages.

"Brio.Portal," product information sheet, 1 page.

"Portal-in-a-Box™," Product Brief, Autonomy Inc., www.automony.com, Apr. 2002, 6 pages.

"Actuate Software," Sun Solutions Catalog, Actuate Corporation & Sun Microsystems, www.sun.com, 2002, 24 pages.

Hazumi et al., "Development of Electronic Medical Record System," NEC Research & Development, vol. 41, No. 1, Jan. 2000, pp. 102-105.

McDonald et al., "The Regenstrief Medical Record System: a quarter century experience," International Journal of Medical Informatics, vol. 54, 1999, pp. 225-253.

"CDR-Web," Reliance Software Systems, Website, 2000, 1 page.

Marietti, "'O' Pioneers!," Healthcare Informatics, Website, May 1999, 9 pages.

Johnson, "Today's CDRs: The Elusive Complete Solution," Healthcare Informatics, (Website), Jul. 1997, 7 pages.

Andrew et al., "Computer-Based Patient Records—Venturing Off the Beaten Path: It's Time to Blaze New CPR Trails," Healthcare Informatics, (Website), May 1997, 17 pages.

"EMR Features," Care Is #1, 1999-2000, 1 page.

"Enterprise Systems Management," Cerner Corporation, www.cerner.com, Sep. 13, 2001, 5 pages.

"HealthMatics™ Office", Healthmatics Office, Website, 3 pages, (date unknown).

CliniComp, Intl., Website, 1999-2000, 1 page.

"ExcelCare Windows", Website, 2 pages (date unknown).

"IC-Chart Information", InteGreat, Website, 1 page, (date unknown).

"Managing mail messages with rules," Microsoft Outlook Help Manual, Website, Version 6, 5 pages Jun. 24, 2002.

Mercando, "Appointment Scheduling on Computer", PACE, vol. 20, Jul. 1997, pp. 1860-1862.

EncounterPRO, the Workflow Enabled CPR/EMR from JMJ Technologies, JMJ Technologies, Inc., www.jmjtech.com, Nov. 8, 2002, 6 pages.

"Expeditor Systems—The Patient Flow Systems Experts", Expeditor Systems, www.expeditor.com, 2001, 3 pages.

"Working with Patient Lists," EpicCare Inpatient Electronic Medical Record Jul. 2000 User's Guide, Epic Systems Corp., Section 10.5-10.6, 3 pages.

"Patient Lists," EpicCare Inpatient Electronic Medical Record Jul. 2000 User's Guide, Epic Systems Corp., Section 11.3-11.4, 3 pages.

"Oacis—Census Management," DINMAR (U.S.) Inc., www.oacis.com, 2002, 2 pages.

Grimson et al., "Interoperability Issues in Sharing Electronic Healthcare Records—the Synapses Approach," IEEE, 1997, pp. 180-185.

"Clinician Documentation with EMR," CliniComp, Intl., www.clinicomp.com, 1999-2002, 1 page.

"Essentris™ CPOE", CliniComp, Intl., www.clinicomp.com, 1999-2002, 2 pages.

"Essentris™ GDR," CliniComp, Intl., www.clinicomp.com, 1999-2002, 2 pages.

"Intensivist Tools," CliniComp, Intl., www.clinicomp.com, 1999-2002, 2 pages.

"CMRxp—Computerized Medical Records Powered by Experience!!," Electronic Medical Records (EMR)xp Experience, Chartcare, Inc., www.chartcare.com, Mar. 5, 2003, 2 pages.

"Dr-InBasket-Lab Results, Messaging and To-Do's," Chartcare, Inc., www.chartcare.com, Mar. 5, 2003, 3 pages.

"PatInfo-Patient Information Handouts," PatInfo-Patient Demographics Software, Chartcare, Inc., www.chartcare.com, Mar. 5, 2003, 2 pages.

"Recall-Patient Health Maintenance," Chartcare, Inc., www.chartcare.com, Mar. 5, 2003, 3 pages.

"LabTrack-Lab Ordering & Results Tracking," LabTrack-Lab Result Tracking Software, Chartcare, Inc., www.chartcare.com, Mar. 5, 2003, 3 pages.

"Rx-MedTrack-Prescription Writing/Medication Tracking," Rx-MedTrack-Prescription Writing Software, Chartcare, Inc., www.chartcare.com, Mar. 5, 2003, 2 pages.

"The Right Tools," Product Description, InteGreat Inc., www.igreat.com, 2003, 1 page.

"IC-Chart Additional Modules," InteGreat Inc., www.igreat.com, 2003, 2 pages.

"Services," InteGreat Inc., www.igreat.com, 2003, 2 pages.

"HCS Order Communications Module," web.archive.org/hcsinteractant.com, 2000, pp. 1-2.

Ebida et al., "Getting Data Out of the Electronic Patient Record: Critical Steps in Building a Data Warehouse for Decision Support," SIMS University Health Network, Dept. of Medicine, University of Toronto, Canada, pp. 1-5.

"Patient1 Vista", PerSe Technologies, www.per-se.com/web.archive.org, 2000, 2 pages.

"Sunrise Clinical Manager", Eclipsys, Sunrise Clinical Overview, www.eclipsnet.com/web.archive.org, 1 page.

"American Medical Management Selects Tandem Computers as Systems Partner", PR Newswire, Feb. 20, 1997, 2 pages.

"Premier Members Select Cerner's Clinical Data Repository as a Result of Exclusive Endorsement", PR Newswire, Feb. 19, 1997, 2 pages.

"Physicians and Staff Go Online with Cerner's Clinical Data Repository and Orders Management", PR Newswire, Mar. 4, 1996, 2 pages.

"Patient1", PerSe Technologies, www.per-se.com/web.archive.org, 2000, 4 pages.

Egan et al., "Computers and Networks in Medical and Healtchare Systems," Comput. Biol. Med., vol. 25, No. 3, 1995, pp. 355-365.

Plaisant et al., "An Infomormation Architecture to Support the Visualization of Personal Histories," Information Processing & Management, vol. 34, No. 5, 1998, pp. 581-597.

Velde, "Framework for a Clinical Information System," International Journal of Medical Informatics, vol. 57, 2000, pp. 57-72.

Fabbretti et al., "Applying the Object Paradigm to a Centralized Database for a Cardiology Division," International Journal of Bio-Medical Computing, vol. 42, 1996, pp. 129-134.

"ICA Technology", Citrix ICA Technology, Interquad Group Limited, www.interquad.com/systems/products/citrix/ICATechnology.shtml, 2004, 3 pages.

"Citrix MetaFrameXP", Citrix MetaFrameXP Product Overview, Interquad Group Limited, www.interquad.com/systems/products/citrix/MetaFrameXP.shtml, 2004, 2 pages.

McDonald, et al., International Journal of Medical Informatics, vol. 54, pp. 225-253, 1999.

Beckham, J, Healthcare Forum Journal, vol. 39, No. 4 Jul./Aug. 1996.

Ho, et al., International Journal of Operations and Production Management, vol. 15, No. 6, 1995.

* cited by examiner

SYSTEM AND METHOD FOR REDUCING THE STEPS INVOLVED IN SEARCHING FOR AVAILABLE APPOINTMENT TIMES AND SCHEDULING APPOINTMENTS IN A HEALTH CARE ENVIRONMENT

CROSS-REFERENCE TO RELATED APPLICATIONS

This application is based on and claims the benefit of U.S. Provisional Application No. 60/645,809, filed Jan. 20, 2005, and incorporated herein by reference.

BACKGROUND OF THE INVENTION

The present invention relates generally to a system and method for searching for available appointment times for scheduling appointments in a health care environment, and more particularly to a system and method for reducing the steps involved in searching for available appointment times using a variety of dynamic appointment options via a plurality of predefined searches for scheduling appointments at the most appropriate appointment times.

Computer programs for appointment scheduling are well known in the art. According to usual procedures, appointments are scheduled by office personnel in response to contacts from patients wanting to schedule appointments. Various computerized scheduling systems have been developed, which facilitate matching patients to available appointment times. However these systems often require many steps to complete the appointment scheduling process. Other prior art software scheduling systems have been developed to reduce the number of steps required for scheduling appointments by copying forward a similar old appointment to make a new appointment just like it, or by jumping into a scheduling application for scheduling a patient from a waiting list. However, these systems have limited uses and applications.

Searching for available appointment times in scheduling appointments in a typical health care environment can be very repetitive. For example, scheduling appointments for routine office visits, physicals, immunizations, flu shots, etc., requires a user to step through several prompts and display screens on a computer of a computerized scheduling system, each time entering data or searching for data, to arrive at a scheduled appointment. FIG. 1 illustrates a flow diagram of the steps required in scheduling an appointment in a health care environment using a typical prior art computerized scheduling system. In a normal computerized appointment scheduling process 10, a user enters the name of the patient into the system 12. The user then enters the type of appointment to be scheduled 14, the name of the patient's primary care physician (PCP) or health care provider 16, and the desired search dates for scheduling the appointment 18. The user may further be required to enter other information, such as insurance coverage, health care provider referrals, or other administrative data. The system then searches the provider's schedule for available appointment time slots for the desired appointment dates 20. If the provider's schedule is too full or the available appointment times are not desirable to the patient, then the user would enter the name of another provider. If the provider's schedule has available appointment time slots, then the user selects the appropriate or desired appointment time 22. The user then reviews the appointment details 24, verifies the appointment with the patient and accepts the appointment 26.

The present invention provides a system and method of searching for and scheduling appointments in a health care environment that is simpler, faster, more user friendly and more efficient than prior art scheduling systems and methods.

SUMMARY OF THE INVENTION

The present invention provides a computerized searching and scheduling system that allows users to search for and schedule appointments within a health care information system and also via the Internet. The purpose of the present invention is to provide users with the ability to search for available appointment times to schedule appointments with a minimal input of information by users. The present invention provides a faster more efficient way of searching for available appointment times and scheduling appointments. It minimizes the need for a person searching for available appointment times and scheduling an appointment to input data, thus significantly increasing scheduling speed, accuracy, efficiency, etc.

The present invention is a computerized searching and scheduling system that makes it easy to search for available appointment times and schedule any type of appointment or procedure from anywhere in a health care organization, including over the Internet. The present invention comprises a search engine that finds the best time or combination of times with the appropriate resources. The search engine preferably uses a sophisticated set of search algorithms to find scheduling solutions, based on a plurality of search definitions, search parameters and multiple passes through a search algorithm. The present invention also leverages the benefits of knowledge known by the health care information system, such as insurance coverage, patient demographics, etc., and automatically applies that information to the appointment being scheduled. The present invention significantly reduces the need for intense user training and user interaction with the searching and scheduling system, as very little information is required to begin a search of available appointment times and to schedule an appointment.

The search engine preferably comprises a plurality of search algorithms, each having a search definition with a plurality of search parameters and search passes predefined for various health care appointments. The present invention allows users to define search parameters and search criteria into search algorithm definitions and make them available to users. The present invention is preferably designed for a variety of visit types, such as physicals, cardiac stress tests, immunizations, flu shots, etc. Visit types can be saved in the search algorithms. Alternatively, a user may be prompted for a visit type that is then loaded into a predefined search algorithm or dynamic search algorithm. The visit type can include complex appointment types that may involve multiple parts, multiple resources, multiple visits and multiple provider types.

The search algorithms allow users to define search parameters in search definitions based on providers, dates, times, etc. Providers are defined as people, resources or any entity with time that can be scheduled. The search algorithms are customizable by users as needed. For example, to schedule a physical, the user would initiate a search to see if the patient's PCP is available. If so, the user will be presented with available times for that provider. If not, user will be presented with available times for the first available provider in the same department as the PCP. Alternatively, a search algorithm may automatically schedule the first available appointment.

Each search algorithm is associated with a record including various fields such as title, department, visit type and status. The search definition preferably includes a plurality of search parameters and search passes with search pass information that will be referred to as the search algorithm is executed. When a search is initiated by a user, a search algorithm is invoked, the user is shown a display of all possible appointment scheduling openings that fall within the search parameters, and the user can then select from those listed openings. In other words, with a single invocation of a search algorithm, one or more valid open appointment times are immediately presented to the user.

As mentioned above, the present invention provides an automatic listing of available appointment scheduling options and any notifications associated with any of the appointment options. Selecting an appointment option may result in immediate scheduling of the appointment, or the continuation of a workflow including health care insurance account selection, referral validation and registration.

Thus, the invocation of a search algorithm takes a user to a list of validated appointment schedule options that can be accepted within seconds. This saves the user from the repetitive work of entering a variety of information several times per day, as is typically required when searching for available appointment times and scheduling appointments.

Most prior art scheduling systems and methods supply default values into appointment fields, but these prior art systems and methods still require users to step through the appointment scheduling process of viewing and accepting data through a plurality of actions encountered in a plurality of different computer screens. The present invention does not require users to enter data or select default values in a plurality of appointment fields. Rather, the present invention bypasses several of the steps required in prior art scheduling systems and methods by immediately providing an appointment solution from minimal user input, such as by inputting the patient's name, selecting the type of appointment to be scheduled or by selecting the appropriate appointment search to be invoked.

Various other features, objects, and advantages of the invention will be made apparent to those skilled in the art from the accompanying drawings and detailed description thereof.

DETAILED DESCRIPTION OF THE INVENTION

The searching and scheduling system and method of the present invention is intended for use with an enterprise health care information system and as a stand-alone computer application program. In the enterprise health care information system embodiment, the searching and scheduling system and method is integrated into the enterprise health care information system and accesses data within the system. The enterprise health care information system preferably comprises a plurality of integrated software applications and allows users to move between the plurality of software applications. The enterprise health care information system preferably includes the computerized searching and scheduling system that makes it easy to search for available appointment times and schedule any type of appointment or procedure from anywhere in a health care organization, including over the Internet. In the stand-alone embodiment, the searching and scheduling system and method accesses data from other applications that may be stored in multiple places, and provides algorithms and an interface for searching available appointment times and scheduling appointment from within a health care organization and over the Internet.

Figure 1:
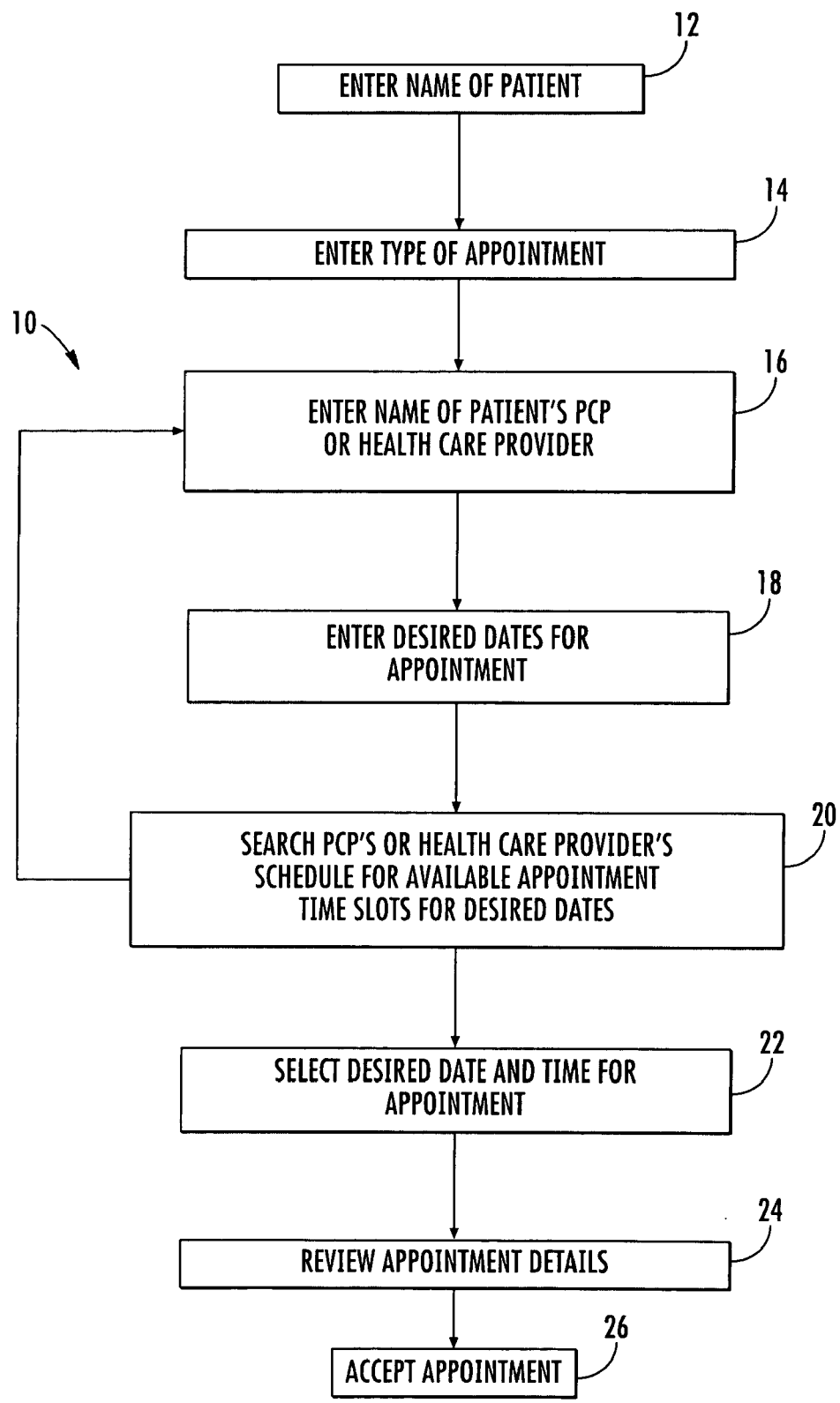
FIG. 1 is a flow diagram of the steps required in scheduling an appointment in a health care environment using a prior art computerized scheduling system.
Figure 2:
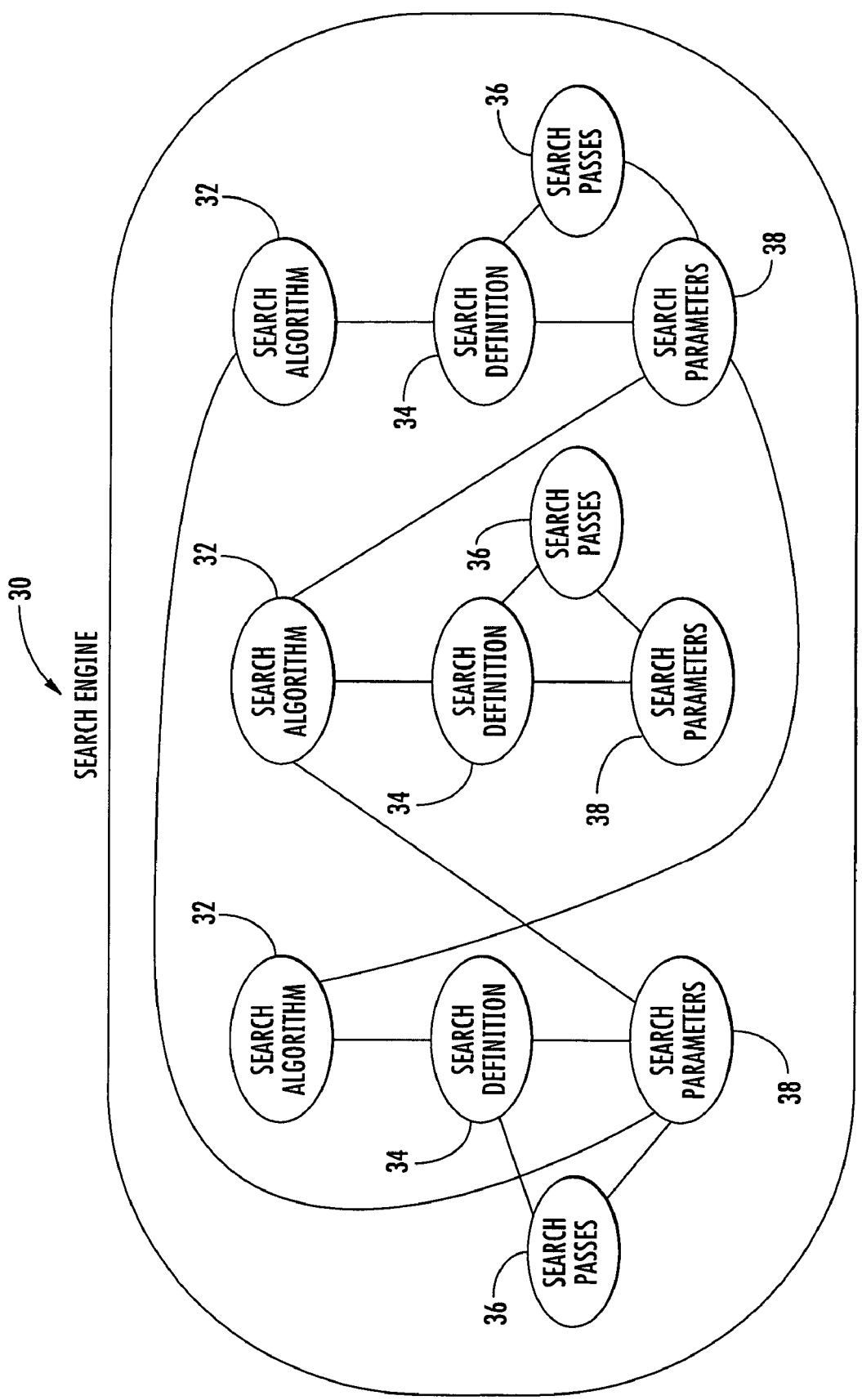
FIG. 2 is a block diagram of the searching and scheduling system of the present invention.

Referring now to the drawings, FIG. 2 is a block diagram of the searching and scheduling system of the present invention. The searching and scheduling system of the present invention preferably comprises a search engine 30 that utilizes predefined parameters to find the best time or combination of available appointment times with the appropriate resources. It uses a sophisticated set of search algorithms 32 to find appointment scheduling solutions, based on search definitions 34 having passes 36 and parameters 38 involving providers, dates, times, etc. Providers are defined as people, resources or anything with time that can be scheduled.

As shown in FIG. 2, the search engine 30 preferably comprises a plurality of search algorithms 32, each having a search definition 34 with a plurality of search parameters 38 and search passes 36 predefined for various health care appointment scheduling options. Each of the search definitions 34 are linked to the search algorithms 32, so that a search definition 34 may link to and/or invoke other search algorithms 32. Once a user invokes a search algorithm 32, the algorithm executes its search definition 34, which may invoke other search algorithms 32, as necessary.

Figure 3:
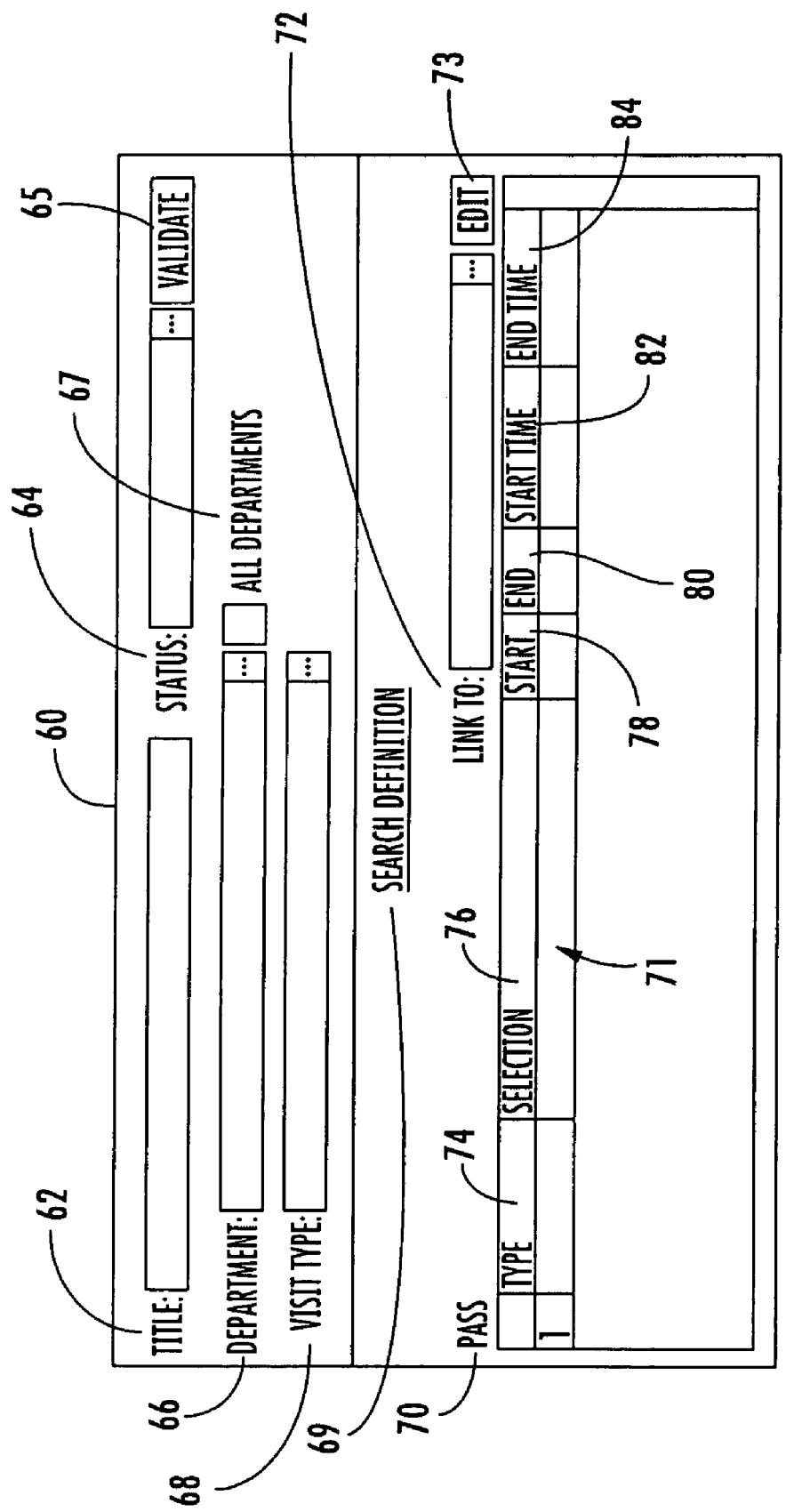
FIG. 3 is an example screen shot of a search algorithm and search definition window in accordance with an embodiment of the present invention.

FIG. 3 is an example screen shot of a search algorithm 60 and search definition 69 window in accordance with an embodiment of the present invention. The search algorithms allow a user to define a plurality of appointment searches based on various parameters, such as providers, dates, times, etc. Each search algorithm 60 preferably includes a record with various fields such as a title 62, a department 66, a visit type 68 and a status 64. The title 62 is the caption shown to the user for a particular search algorithm. The department 66 is the department(s) where the search algorithm will be shown. A user may select all departments 67. The visit type 68 is the appointment visit type used for the search algorithm. The visit type 68 can include complex appointment types that may involve multiple parts, multiple resources, multiple visits and multiple provider types. The status 64 is the status of the record for the search algorithm. The status 64 provides an indication of whether the search algorithm is valid and ready to be used or not. Preferably, the status 64 will either be "Active" or "In-Active," as set by a user. Other status parameters may include "not taking new patients" and other intermediates between "Active" and "In-Active." Changes to a search algorithm will cause the search algorithm to be "In-Active" until the user validates 65 the record. Other fields that may be included in the search algorithm record include, but are not limited to, an "override schedule workflow" that allows administrators to override the default schedule workflow, an "audit trail" that is a listing of all actions performed on the record and "administration notes" which is free text associated with the search algorithm. Once a user begins the process of scheduling an appointment, the search algorithms are executed to determine a plurality of available openings for an appointment that meet the search criteria defined in the algorithm. The user then sees a display of all available appointment openings that meet the search criteria.

As an example, a search algorithm can be defined to include a certain type of procedure that needs to be scheduled two weeks out. When scheduling an appointment for that procedure, the search algorithm will automatically look two weeks out to schedule an appointment. The scheduling solutions found may not be the first solutions in time order that are available, but it may depend on other parameters such as the availability of the health care providers and resources required by the procedure, and patient preferences.

In another example, a search algorithm can be defined to include providers from an academic institution with a large number of faculty specialists and residents. If the faculty specialists want the residents to take the appointments before they do, then the search can be defined to schedule appointments with the residents in a first pass for a specific period of time, and if there is no appointment available in that pass, a second pass will allow appointments to be scheduled with the faculty specialists.

Figure 4:
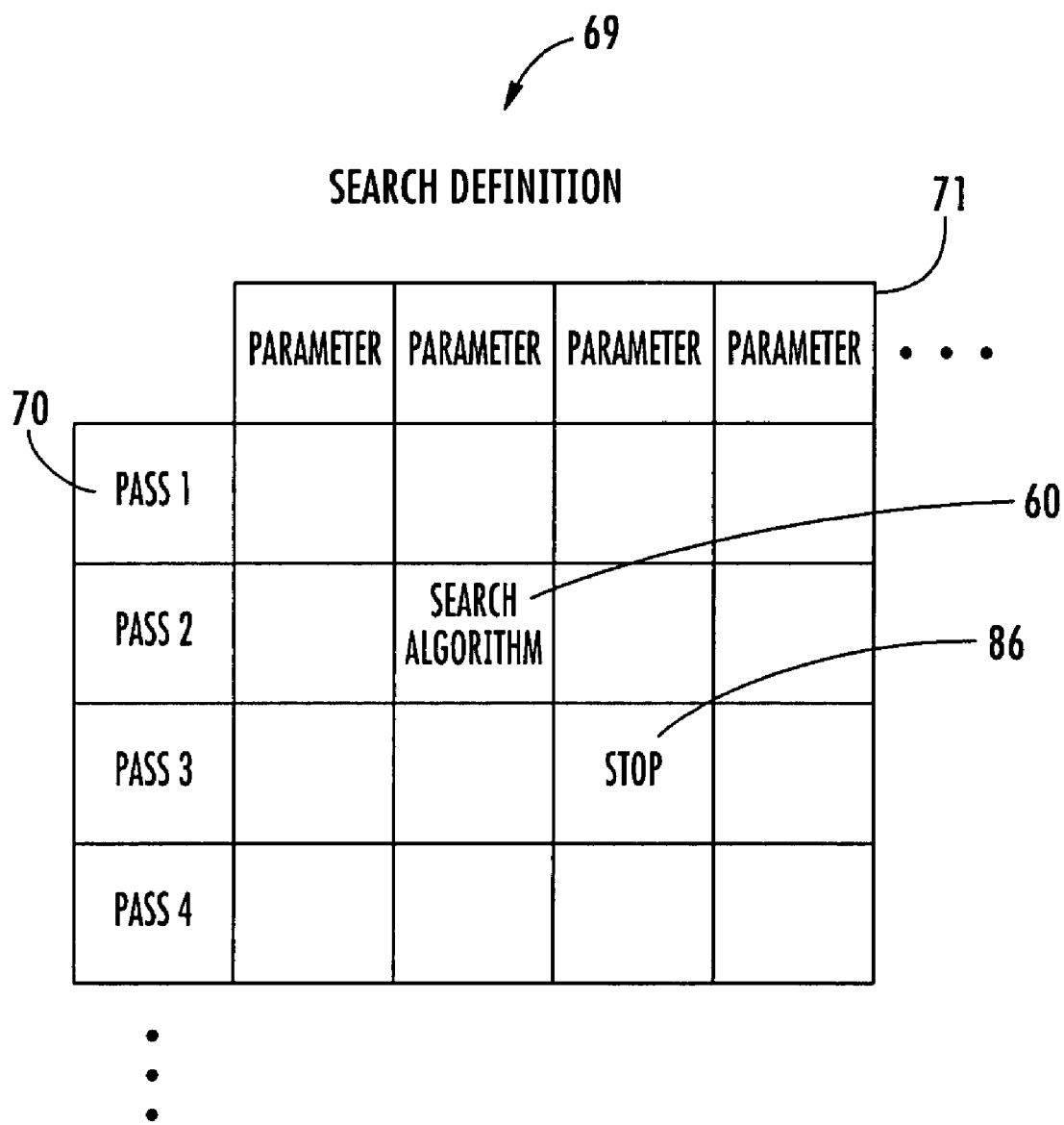
FIG. 4 is a table illustrating a search definition of the present invention.

Referring to FIGS. 3 and 4, the search definition 69 preferably includes a plurality of search passes 70 and search parameters 71 with search information that will be referred to as the search algorithm 60 is executed. The search definition 69 preferably includes various parameters 71 for defining the search algorithm 60 that is used in searching for available appointment times and scheduling appointments. The search definition 69 allows for easy customization of the search parameters that will search a plurality of schedules to allow for an appointment scheduling solution to be presented to the user indicating that a single, a plurality or no appointment options are available.

As mentioned above, the search definition 69 preferably includes a plurality of different passes 70 for each search algorithm 60, based on provider selection, date selection, time selection or any other search parameter 71 defined within the search definition. Each pass 70 defines the order the search algorithm uses to search. Examples of parameters 71 used in the search definition include a type of provider selection 74, an actual provider selection 76, a start date 78 or start date offset where the algorithm starts the search, an end date 80 or end date offset where the algorithm ends the search, a days of the week parameter which shows only solutions on certain days of the week, a start time 82 which is the time of day where the search begins, an end time 84 which is the time of day where the search ends, an exact length parameter which shows time slot solutions that match the visit length exactly, a stop 86 which may be included in a pass to stop the search. If a pass is marked with a stop, then the search will not continue on to another pass if the current pass or any other previous pass has found a scheduling solution. A time or day offset is defined as a period of time that is offset from a predefined time or day. Other examples of parameters used in the search definition may include an overbooking parameter which would include slots that a user would have to "overload" to use, a respect session limits parameter which respects defined session limits for a given visit type, time frame, provider or department, a maximum scheduled utilization parameter which shows scheduling solutions from dates with schedule utilization less than or equal to this predefined value, a patient preferences parameter which shows scheduling solutions that match patient preferences, an in network parameter which shows scheduling solutions from in network providers, an all slots parameter which shows all blocked and unblocked slots, a block parameter that shows only the slots within a specified block. The block parameter can be left blank to indicate unblocked slots. The visit type entered in the search algorithm will be allowed to be scheduled into the block entered regardless of any setup limitations.

The search definition pass criteria also preferably includes a pass parameter that provides a list of providers to search. It is preferable to build a list of target health care providers to search, and list them in the order that they will be searched according to pass numbers. The list of providers may be organized in pools or group of providers, an entire department of providers, individual providers, current PCPs, etc. The pass criteria preferably includes one or more different passes in the searching hierarchy that are searched in order to provide an appointment scheduling solution. For example, the first pass might be a nursing pool; the second pass might be a doctor pool, etc. When accomplishing the search, the search algorithm goes through the first pass completely, generates all the possibilities for the first pass according to the search algorithm, and then moves on to the second pass, generating all the possibilities for the second pass according to the search algorithm. A pass 70 can also include a search algorithm 60, as shown in FIG. 4. For example, the first pass may be a search definition, the second pass may be a separate search definition, and the third pass may be a combination of search definitions that include one or more search algorithms. One search algorithm may invoke another algorithm automatically, if a search algorithm is in a search definition. It is also possible to have a chain of passes with search algorithms nesting within other search algorithms.

The pass criteria also preferably includes a user-defined provider selection that may include a selection of individual providers, groupings of providers, subgroups, departments, specialties, and wildcard types (such as PCPs or other user selected wildcard types). The user must choose a selection type and then make a selection from within that type. For example, the type may be a "Subgroup" and the selection may be "Female Providers."

Groupings of providers can be defined in the search definition, such as a predefined list of principal providers or providers that share a specific relationship. For example, the pre-defined list may include providers in a department, all providers in a department, user specific criteria such as any providers in a department, or role specific criteria such as all providers at a clinic with a clinic specialty. These examples are meant to illustrate the customization capabilities of the search algorithms. Other criteria and searches can be defined as one skilled in the art will recognize. Any possible grouping of providers is allowed.

Examples of provider selections include individual providers, groupings of providers, subgroups of providers which can be defined as group of providers that can be defined differently in different departments. For example, a female provider subgroup will be different in each department. Other provider selections may include all providers in a specific department, all providers from all departments with a certain specialty defined, a patient's defined PCP (wildcard), a patient's defined PCP's team (wildcard), all providers in the user's current department (wildcard) based on user context, and a patient's defined care team (wildcard).

The pass criteria may also include start dates, end dates, start times and end times for searching in conjunction with the health care provider types and selections. Any openings within those parameters will result in a listing of available appointment dates and times for a user to choose from. This can also be not limited to dates and times.

The search definition also preferably includes a link 72, see FIG. 3, to other search algorithms. A link 72 allows the use of other algorithm search definitions. A user can display of all the records linked to the current record. Each search algorithm has its own search record definition, but linking to another search algorithm is allowed to provide compatibility and reduce maintenance overhead. For example, there may be a plurality of search algorithms, one in two different departments that follow the same basic rules and logic. The rules can be defined so that a different title or visit type is displayed based on the context of the user. If the same search definition is used, a user can link to a different search algorithm. As a result, the search algorithm would only need to be built once, stored in one location, and updated in one place.

The link functionality is useful for searching and scheduling appointments that have the same parameters but different names in different contexts. For example, in one clinic or department, an appointment may be called a "school physical visit," whereas in another clinic or department the same appointment may be called a "well child visit." The search definition references the appropriate visit type, allowing the same search to be performed across multiple departments and providers. The link 72 may be edited 73 by a user.

The pass criteria also preferably includes a block parameter for excluding certain health care providers, pools, groups and departments from the search definition. A block is a limitation on a time slot, i.e., from 10:00 to 10:30 only office visits or consults may be scheduled and from 10:30 to 11:00 only follow-up visits may be scheduled. The ability to define that only certain slot types should be searched. The search algorithm may include or exclude certain providers, pools, groups and departments from the search algorithm. A user preference functionality is preferably included in the search definition that provides the ability to include user preferences into the search algorithms. A point of service (POS) functionality is also preferably included in the search definition to allow filtering of appointment options based on referral requirements, network participation and covered services based on information stored in the system.

The search algorithms of the present invention preferably have the capability to include referral tracking into the search definition. In this embodiment, a user can enter complete information for each referral from a health care provider to a specialist or another clinician. The search definition would preferably include but not be limited to a clinician or specialty referred to, a listing of procedures requested, the diagnosis, etc. The system would preferably store the authorization in the referral record, including the number of visits authorized, authorizing staff, expiration date, and authorization numbers. The system would also preferably provide a number of options for notifying providers of referral activities, including automatic notification to the PCP upon approval or denial of the referral. Once all referral information has been entered, per the organizations guidelines, scheduling options could automatically be presented by the system based on the information entered. A search algorithm can be attached to orders, referrals or anything else. An order may be defined as something a provider orders. A referral may be defined as a request for an appointment.

The search algorithms of the present invention preferably also have the capability to include eligibility tracking into the search definition. In this embodiment, the system would preferably track eligibility information for each patient based on health care plans, including coverage effective and expiration dates, and maintain a history of a patient's active and inactive coverages.

The search algorithms provide all of the filtering required for searching for and scheduling an appointment. The search algorithms are completely configurable, based on the search definitions provided by the users. Any number of different restrictions are available when scheduling appointments. The system pre-screens all available dates and times for any notifications or restrictions defined in the search algorithms. The system also provides a plurality of notifications for a scheduled appointment depending on how the search is defined. For example, a user can define time slots in the search definition that are not available for scheduling appointments. Therefore, if a user tried to schedule an appointment under one of the unavailable time slots, a warning would be displayed to notify the user that the desired time slot is unavailable. Time slots can be also limited such that only certain types of appointments, such as consult appointments, can be scheduled into them. These time slots would be presented when a search algorithm searched for consult visits, but not for other visit searches. Further, users may have different levels of security, and a user with higher security may be presented with different results based on their security. A user may only be shown a limited set of results, whereas a more flexible rule interpretation may be allowed for a provider scheduling into their own schedule.

Other items that may be integrated into the search include but are not limited to patient preferences, days of week, referral validation, automatic network filtering (checking provider participation in a patient's insurance coverage), etc. In this expanded workflow, the users may again be returned to the listing of available times that meet the search criteria. The user then selects the desired time and the appointment is scheduled.

The search options presented to a user are automatically filtered based on user characteristics and context. User characteristics may include the user's position in the organization, such as whether or not the user is a supervisor, scheduler, nurse, etc. User context may include things such as the department or facility that the user is currently logged in to. In addition, the search options presented to a user may be filtered based on security. For example, certain users may only be able to access certain types of searches. If a level of security is required to schedule certain types of visits and the user doesn't have the required security, than that user cannot initiate a search for those types of visits. The searches presented to a user may also be filtered based on patient characteristics. For example, if a user is scheduling an appointment for a male patient, a search for a pap smear appointment or a pregnancy visit would not be shown.

The system of the present invention is preferably designed to come up with as many available dates and times for an appointment, based on the search definitions and search algorithms provided by the user. The appointment solution preferably includes the patient's name, a listing of available dates, a listing of available times and a selection for choosing the desired time for the appointment. Once a time is selected, notifications will be displayed, if any, followed by a confirmation of the scheduled appointment.

Figure 5:
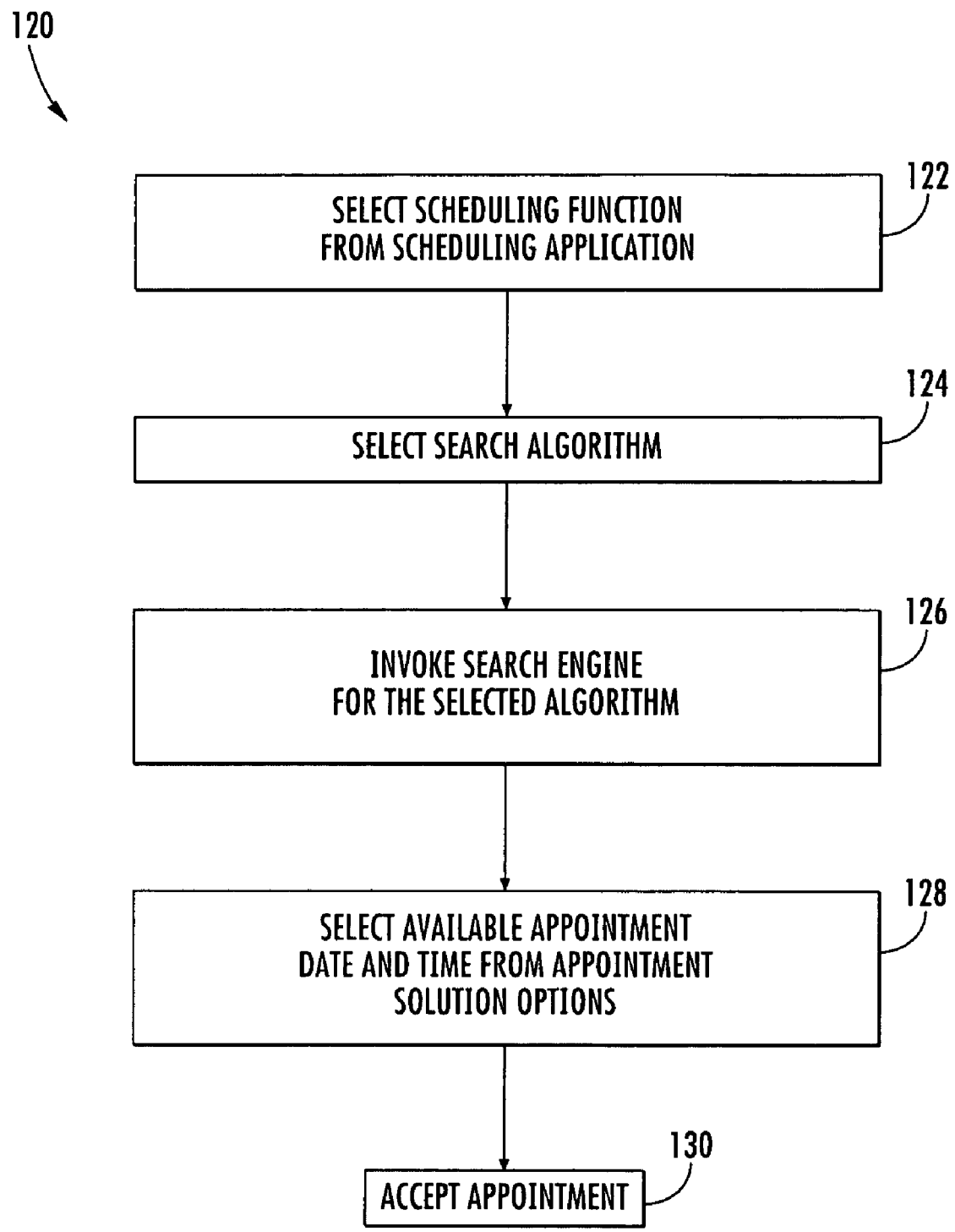
FIG. 5 is a flow diagram of the steps required in searching for and scheduling an appointment in a health care environment in accordance with an embodiment of the present invention.

FIG. 5 is a flow diagram 120 of the steps required in searching for and scheduling an appointment in a health care environment in accordance with an embodiment of the present invention. In the appointment scheduling process, a user typically receives a phone call or email from a patient wanting to schedule an appointment. The user selects the scheduling function from the scheduling application activities program 122 of the present invention to open the appointment scheduling process. In the scheduling function, the user selects the appointment function. This will bring the user to a prompt to enter information about the patient and/or the appointment to be scheduled. The user then enters the patient's name or selects it from a list of patients. Alternatively, a user already accessing a patient record may select the appointment function and move directly to the scheduling flow for the patient with which they are working. A drop down menu or other similar graphical user interface, makes the appointment options defined in the search definitions available to the user based on the user's context (such as the department they are in, the type of medicine practiced at their clinic, etc.). Other methods of displaying appointment information for the active search algorithms may be implemented, as one skilled in the art will appreciate. The user selects the desired search algorithm 124 from a list of search algorithms and launches or invokes the search engine for the selected search algorithm 126, including an available times activity function using the associated search algorithm, displaying the available appointment dates and times, and any notifications. If no notifications are displayed or the user accepts the notifications, the system may jump to a health care insurance account selection using current patient and appointment type if this information is needed, needs to be updated, or is otherwise not already available in the system. The available time activity function appears with pre-screened openings that match the search criteria and rules in the search algorithm. The available time activity function provides a listing of the available dates and times. The user then selects an available appointment date and time 128, accepts the appointment 130 and the appointment is scheduled. The system provides for confirmation of the scheduled appointment and a way to select an alternate appointment, if necessary. It is possible for a user to "back-up" through the steps of the scheduling process at any appointment, preventing the need for a user to start over if a mistake occurs or an appointment parameter changes.

Figure 6:
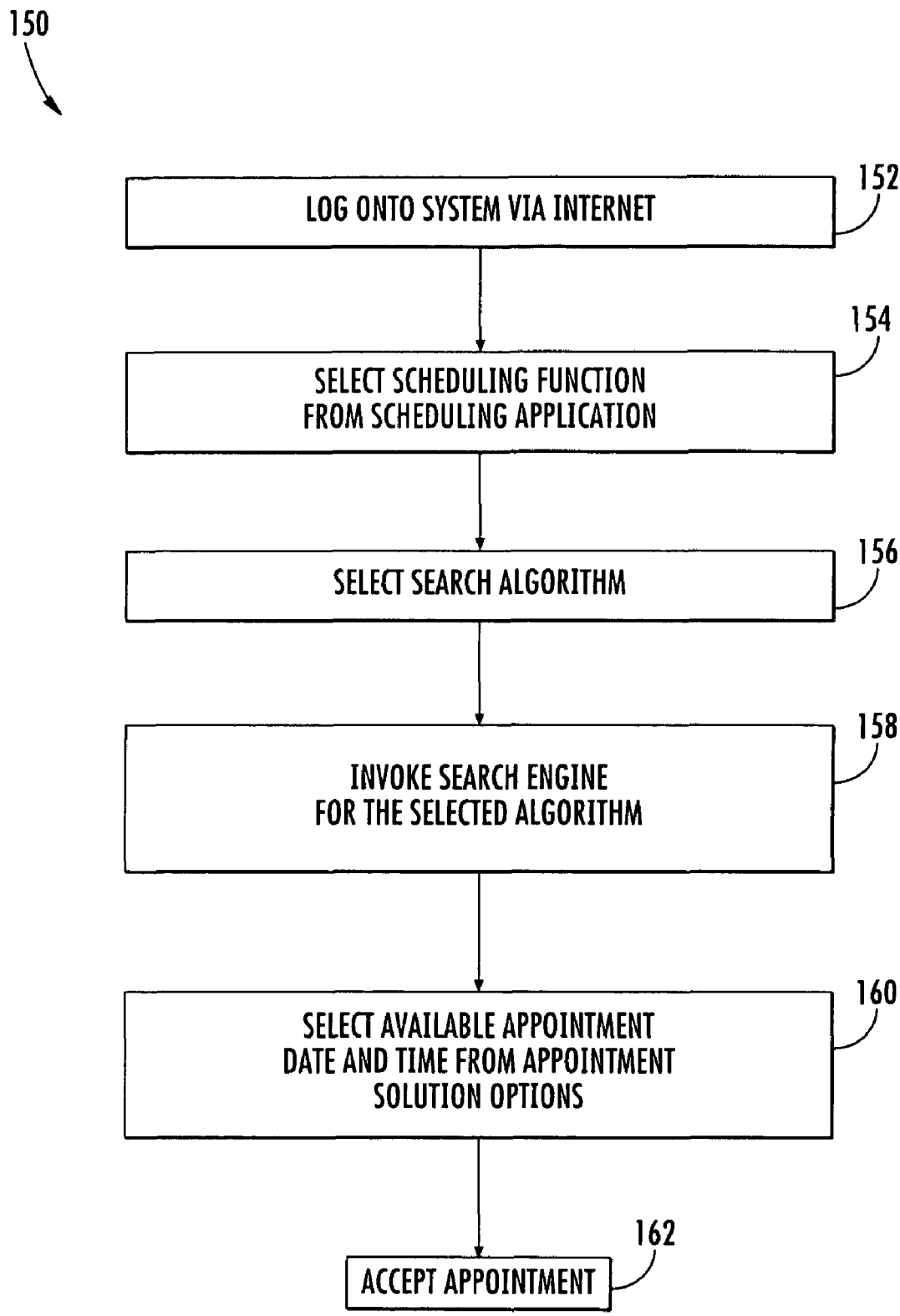
FIG. 6 is a flow diagram of the steps required in searching for and scheduling an appointment in a health care environment over the Internet in accordance with another embodiment of the present invention.

FIG. 6 is a flow diagram 150 of the steps required in searching for and scheduling an appointment in a health care environment over the Internet in accordance with another embodiment of the present invention. In this embodiment, the system of the present invention can be used by internal and external users via the Internet. For example, users would access the present invention to schedule appointments via an Internet browser or an intranet browser. An example of an external user would be a health care provider referring a patient to a hospital or clinic.

The appointment scheduling function of the present invention is available over the Internet. The entire appointment scheduling workflow is integrated into an Internet browser. The present invention is accessible by both internal and external users. In the appointment scheduling process over the Internet, a user logs onto the system via the Internet 152. The user then selects a scheduling function from the scheduling application activities program 154 of the present invention to open the appointment scheduling process. In the scheduling function, the user selects the appointment function. This will bring the user to a patient prompt. The user then enters the patient's name or selects it from a list of patients. Alternatively, a user already accessing a patient record may select the appointment function and move directly to the scheduling flow for the patient with which they are working. A drop down menu or other similar graphical user interface is displayed listing a plurality of appointment type options. The user selects the desired search algorithm 156 from a list of search algorithms. This launches or invokes the search engine for the selected search algorithm 158, including an available times activity function using the associated search algorithm, displaying the available appointment dates and times. The user then selects the desired appointment date and time 160. After an available appointment option is selected, the user then sees a page that displays any notification messages about the appointment they are trying to schedule, if any. External users will also be able to specify a referring health care provider for the appointment if necessary or desired. Once the user accepts the notifications, if any, and optionally enters a referring health care provider, the appointment is accepted 162. The user then receives a confirmation of the scheduled appointment. The user may also optionally receive a configurable report that is designed to be given to the patient and preferably displays information about the appointment that is desirable to the patient. The system can be configured to optionally add a configurable note to the scheduled appointment, stating that the appointment was made by an external user. In some embodiments, following appointment creation and confirmation by an external provider may also trigger a message to be sent to schedulers or the provider with whom the patient has been scheduled, or other users as configured in the system.

As another example of this embodiment, an affiliate provider logs into a hospital's system via the Internet. The user selects the health care department that they want to log into. The user then selects a scheduling function icon to open the scheduling function. The user then selects an appointment scheduling function from a drop down menu or other similar graphical user interface of the scheduling function. The user then selects or enters the patient's name. The user selects the type of appointment to be scheduled. A listing of available dates and times is displayed. The user then selects the desired time from the list. At this point, the user may enter a referring health care provider, which is optional. The user then accepts the appointment and receives confirmation of the scheduled appointment. This embodiment makes it very easy for affiliates to refer patients to a hospital.

In another embodiment, the present invention provides the ability to search for appointment records and generate reports from those records. For example, a user may want to search for physicals examinations for a certain patient, and receive a report for those appointments.

While the invention has been described with reference to preferred embodiments, those skilled in the art will appreciate that certain substitutions, alterations and omissions may be made to the embodiments without departing from the spirit of the invention. Accordingly, the foregoing description is meant to be exemplary only, and should not limit the scope of the invention as set forth in the following claims.

What is claimed is:

1. A non-transitory computer-readable medium having stored thereon computer-readable instructions that when executed by one or more computing devices cause the one or more computing devices to:

control presentation of a search definition window, wherein the search definition window includes a first pass definition section and a second pass definition section, wherein the first pass definition section includes a first search parameter input interface for entering a first parameter of a plurality of search parameters defining characteristics for identifying an appointment and the second pass definition section includes a second search parameter input interface for entering a second parameter of the plurality of search parameters defining characteristics for identifying the appointment;

receive a first parameter indicator identified using the first search parameter input interface;

receive a second parameter indicator identified using the second search parameter input interface;

store a search definition including the received first parameter indicator and the received second parameter indicator;

control presentation of a plurality of appointment types from which a user can select an appointment type for scheduling a new appointment, wherein an appointment type of the plurality of appointment types is associated with the stored search definition;

receive an indicator of the appointment type selected from the plurality of appointment types; and execute a search engine to search an appointment database to identify one or more appointments satisfying the stored search definition, wherein the search engine performs a first pass using the received first parameter indicator and performs a second pass using the received second parameter indicator to identify the one or more appointments, wherein the order of performance of the first pass and the second pass is user selectable using the search definition window.

2. The non-transitory computer-readable medium of claim 1, wherein the search definition window further includes a title interface window, and the computer-readable instructions further cause the one or more computing devices to receive a title based on text entered in the title interface window, wherein the title is used to identify the appointment type in the presented plurality of appointment types.

3. The non-transitory computer-readable medium of claim 1, wherein the search definition window further includes a department selector for selecting a medical department associated with the search definition, and the computer-readable instructions further cause the one or more computing devices to receive a department indicator based on a selection from the department selector wherein the stored search definition includes the received department indicator.

4. The non-transitory computer-readable medium of claim 1, wherein the search definition window further includes a visit type selector for selecting a visit type associated with the search definition, and the computer-readable instructions further cause the one or more computing devices to receive a visit type indicator based on a selection from the visit type selector.

5. The non-transitory computer-readable medium of claim 1, wherein the search definition window further includes a status selector for selecting a status of the search definition, and the computer-readable instructions further cause the one or more computing devices to receive a status indicator based on a selection from the status selector.

6. The non-transitory computer-readable medium of claim 1, wherein the search definition window further includes a validate selector, and the computer-readable instructions further cause the one or more computing devices to determine if the search definition is valid upon selection of the validate selector.

7. The non-transitory computer-readable medium of claim 1, wherein the plurality of search parameters includes a provider to search for an appointment.

8. The non-transitory computer-readable medium of claim 1, wherein the plurality of search parameters includes a plurality of provider types, wherein the first search parameter input interface presents a provider based on a selection from the plurality of provider types.

9. The non-transitory computer-readable medium of claim 8, wherein the plurality of provider types includes at least one of an individual provider type, a group provider type, a sub-group provider type, a department provider type, a specialty provider type, and a primary care physician type.

10. The non-transitory computer-readable medium of claim 8, wherein the provider includes a group of providers.

11. The non-transitory computer-readable medium of claim 1, wherein the plurality of search parameters includes a date.

12. The non-transitory computer-readable medium of claim 11, wherein the date includes a start date for searching for the appointment.

13. The non-transitory computer-readable medium of claim 11, wherein the date includes an end date for searching for the appointment.

14. The non-transitory computer-readable medium of claim 1, wherein the plurality of search parameters includes a time.

15. The non-transitory computer-readable medium of claim 14, wherein the time includes a start time for searching for the appointment.

16. The non-transitory computer-readable medium of claim 14, wherein the time includes an end time for searching for the appointment.

17. The non-transitory computer-readable medium of claim 1, wherein the plurality of search parameters includes a stop parameter, wherein selection of the stop parameter indicates that the search engine stop searching the appointment database if one or more appointments have been identified in a previous pass.

18. The non-transitory computer-readable medium of claim 1, wherein the plurality of search parameters includes a link to a second search definition, wherein the search engine further searches the appointment database to identify one or more second appointments satisfying the second search definition.

19. The non-transitory computer-readable medium of claim 1, wherein the computer-readable instructions further cause the one or more computing devices to control presentation of a report including the identified one or more appointments satisfying the stored search definition.

20. The non-transitory computer-readable medium of claim 19, wherein the computer-readable instructions further cause the one or more computing devices to receive a selected appointment indicator identifying a selected appointment selected from the identified one or more appointments satisfying the stored search definition.

21. The non-transitory computer-readable medium of claim 20, wherein the computer-readable instructions further cause the one or more computing devices to store information associated with the selected appointment in the appointment database.

22. The non-transitory computer-readable medium of claim 20, wherein the computer-readable instructions further cause the one or more computing devices to control presentation of a notification related to the selected appointment.

23. The non-transitory computer-readable medium of claim 20, wherein the computer-readable instructions further cause the one or more computing devices to control presentation of a provider message associated with the selected appointment.

24. The non-transitory computer-readable medium of claim 20, wherein the computer-readable instructions further cause the one or more computing devices to control presentation of a scheduling instruction associated with the selected appointment.

25. The non-transitory computer-readable medium of claim 20, wherein the computer-readable instructions further cause the one or more computing devices to control presentation of a referral requirement alert associated with the selected appointment.

26. The non-transitory computer-readable medium of claim 20, wherein the computer-readable instructions further cause the one or more computing devices to control presentation of an out-of-network notification associated with the selected appointment.

27. The non-transitory computer-readable medium of claim 20, wherein the computer-readable instructions further cause the one or more computing devices to control presentation of a non-covered service notification associated with the selected appointment.

28. The non-transitory computer-readable medium of claim 20, wherein the computer-readable instructions further cause the one or more computing devices to track referral information associated with the selected appointment.

29. The non-transitory computer-readable medium of claim 1, wherein the plurality of search parameters includes an overbooking parameter, wherein selection of the overbooking parameter indicates that the search engine can identify one or more appointments that require that the one or more appointments be overbooked.

30. The non-transitory computer-readable medium of claim 1, wherein the plurality of search parameters includes a block parameter, wherein selection of the block parameter indicates that the search engine exclude a selected provider.

31. The non-transitory computer-readable medium of claim 30, wherein the selected provider includes at least one of an individual provider, a provider pool, a provider group, and a provider department.

32. The non-transitory computer-readable medium of claim 1, wherein the presented plurality of appointment types is filtered based on user information.

33. The non-transitory computer-readable medium of claim 32, wherein the user information includes at least one of a user position, a user department, a user facility, and a user security level.

34. The non-transitory computer-readable medium of claim 1, wherein the presented plurality of appointment types is filtered based on a patient characteristic for which the one or more appointments is identified.

35. The non-transitory computer-readable medium of claim 1, wherein the presented plurality of appointment types is filtered by a user.

36. The non-transitory computer-readable medium of claim 1, wherein the plurality of search parameters includes a patient preference parameter.

37. The non-transitory computer-readable medium of claim 1, wherein the search engine further determines if the one or more appointments satisfies eligibility criteria associated with a patient for which the one or more appointments is identified.

38. A system comprising:
a processor; and
a non-transitory computer-readable medium having stored thereon computer-readable instructions that when executed by the processor cause the system to
control presentation of a search definition window, wherein the search definition window includes a first pass definition section and a second pass definition section, wherein the first pass definition section includes a first search parameter input interface for entering a first parameter of a plurality of search parameters defining characteristics for identifying an appointment and the second pass definition section includes a second search parameter input interface for entering a second parameter of the plurality of search parameters defining characteristics for identifying the appointment;
receive a first parameter indicator identified using the first search parameter input interface;
receive a second parameter indicator identified using the second search parameter input interface;
store a search definition including the received first parameter indicator and the received second parameter indicator;
control presentation of a plurality of appointment types from which a user can select an appointment type for scheduling a new appointment, wherein an appointment type of the plurality of appointment types is associated with the stored search definition;
receive an indicator of the appointment type selected from the plurality of appointment types; and
execute a search engine to search an appointment database to identify one or more appointments satisfying the stored search definition, wherein the search engine performs a first pass using the received first parameter indicator and performs a second pass using the received second parameter indicator to identify the one or more appointments, wherein the order of performance of the first pass and the second pass is user selectable using the search definition window.

39. The system of claim 38, wherein the search definition window further includes a title interface window, and the computer-readable instructions further cause the system to receive a title based on text entered in the title interface window, wherein the title is used to identify the appointment type in the presented plurality of appointment types.

40. The system of claim 38, wherein the search definition window further includes a department selector for selecting a medical department associated with the search definition, and the computer-readable instructions further cause the system to receive a department indicator based on a selection from the department selector wherein the stored search definition includes the received department indicator.

41. The system of claim 38, wherein the search definition window further includes a visit type selector for selecting a visit type associated with the search definition, and the computer-readable instructions further cause the system to receive a visit type indicator based on a selection from the visit type selector.

42. The system of claim 38, wherein the search definition window further includes a status selector for selecting a status of the search definition, and the computer-readable instructions further cause the system to receive a status indicator based on a selection from the status selector.

43. The system of claim 38, wherein the search definition window further includes a validate selector, and the computer-readable instructions further cause the system to determine if the search definition is valid upon selection of the validate selector.

44. The system of claim 38, wherein the plurality of search parameters includes a provider to search for an appointment.

45. The system of claim 38, wherein the plurality of search parameters includes a plurality of provider types, wherein the first search parameter input window presents a provider based on a selection from the plurality of provider types.

46. The system of claim 45, wherein the plurality of provider types includes at least one of an individual provider type, a group provider type, a subgroup provider type, a department provider type, a specialty provider type, and a primary care physician type.

47. The system of claim 38, wherein the plurality of search parameters includes a date.

48. The system of claim 38, wherein the plurality of search parameters includes a time.

49. The system of claim 38, wherein the plurality of search parameters includes a stop parameter, wherein selection of the stop parameter indicates that the search engine stop searching the appointment database if one or more appointments have been identified in a previous pass.

50. The system of claim 38, wherein the plurality of search parameters includes a link to a second search definition, wherein the search engine further searches the appointment database to identify one or more second appointments satisfying the second search definition.

51. The system of claim 38, wherein the computer-readable instructions further cause the system to control presentation of a report including the identified one or more appointments satisfying the stored search definition.

52. The system of claim 51, wherein the computer-readable instructions further cause the system to receive a selected appointment indicator identifying a selected appointment selected from the identified one or more appointments satisfying the stored search definition.

53. The system of claim 52, wherein the computer-readable instructions further cause the system to store information associated with the selected appointment in the appointment database.

54. The system of claim 52, wherein the computer-readable instructions further cause the system to control presentation of a notification related to the selected appointment.

55. The system of claim 52, wherein the computer-readable instructions further cause the system to control presentation of a provider message associated with the selected appointment.

56. The system of claim 52, wherein the computer-readable instructions further cause the system to control presentation of a scheduling instruction associated with the selected appointment.

57. The system of claim 52, wherein the computer-readable instructions further cause the system to control presentation of a referral requirement alert associated with the selected appointment.

58. The system of claim 52, wherein the computer-readable instructions further cause the system to control presentation of an out-of-network notification associated with the selected appointment.

59. The system of claim 52, wherein the computer-readable instructions further cause the system to control presentation of a non-covered service notification associated with the selected appointment.

60. The system of claim 52, wherein the computer-readable instructions further cause the system to track referral information associated with the selected appointment.

61. The system of claim 38, wherein the plurality of search parameters includes an overbooking parameter, wherein selection of the overbooking parameter indicates that the search engine can identify one or more appointments that require that the one or more appointments be overbooked.

62. The system of claim 38, wherein the plurality of search parameters includes a block parameter, wherein selection of the block parameter indicates that the search engine exclude a selected provider.

63. The system of claim 38, wherein the presented plurality of appointment types is filtered based on user information.

64. The system of claim 38, wherein the presented plurality of appointment types is filtered based on a patient characteristic for which the one or more appointments is identified.

65. The system of claim 38, wherein the search engine further determines if the one or more appointments satisfies eligibility criteria associated with a patient for which the one or more appointments is identified.

* * * * *